United States Patent [19]

Clarke et al.

[11] Patent Number: 5,064,420
[45] Date of Patent: Nov. 12, 1991

[54] EYELID OPENER

[75] Inventors: Gerald P. Clarke; Jean Keen, both of Oshkosh, Wis.

[73] Assignee: KC Medical Industries Corporation, Oshkosh, Wis.

[21] Appl. No.: 615,802

[22] Filed: Nov. 16, 1990

[51] Int. Cl.$^5$ ............................................. A61M 35/00
[52] U.S. Cl. ..................................... 604/295; 604/301
[58] Field of Search ........................ 604/295, 306–362, 604/294, 296–299; 128/847, 858, 869

[56] References Cited

U.S. PATENT DOCUMENTS

| 3,392,725 | 7/1968 | Behney | 604/301 |
| 4,088,750 | 4/1978 | Bosshold | 604/302 |
| 4,543,096 | 9/1988 | Keene | 604/300 |

FOREIGN PATENT DOCUMENTS

| 2142829 | 1/1985 | United Kingdom | 604/295 |

Primary Examiner—Randall L. Green
Assistant Examiner—K. Reichle
Attorney, Agent, or Firm—Donald Cayen

[57] ABSTRACT

An eyelid opener is useful for opening a person's eye in order to dispense an ophthalmic fluid into the eye. The eyelid opener comprises a collar having internal lobes arranged to enable the collar to be screwed onto the threads of an ophthalmic bottle. A shoulder extends across the collar and limits the engagement of the collar on the bottle threads. The bottle tip passes through a hole in the shoulder. To the collar are joined a pair of flexible wings. The two wings terminate in respective flanges sized and shaped to conform to substantially the length of the exteriors of the human eyelids. The wings can be squeezed together and placed on the eyelids. Releasing the wings causing them to return to their undeflected configurations and thereby open the eye. Then a drop of fluid in the bottle can be dispensed into the open eye.

9 Claims, 1 Drawing Sheet

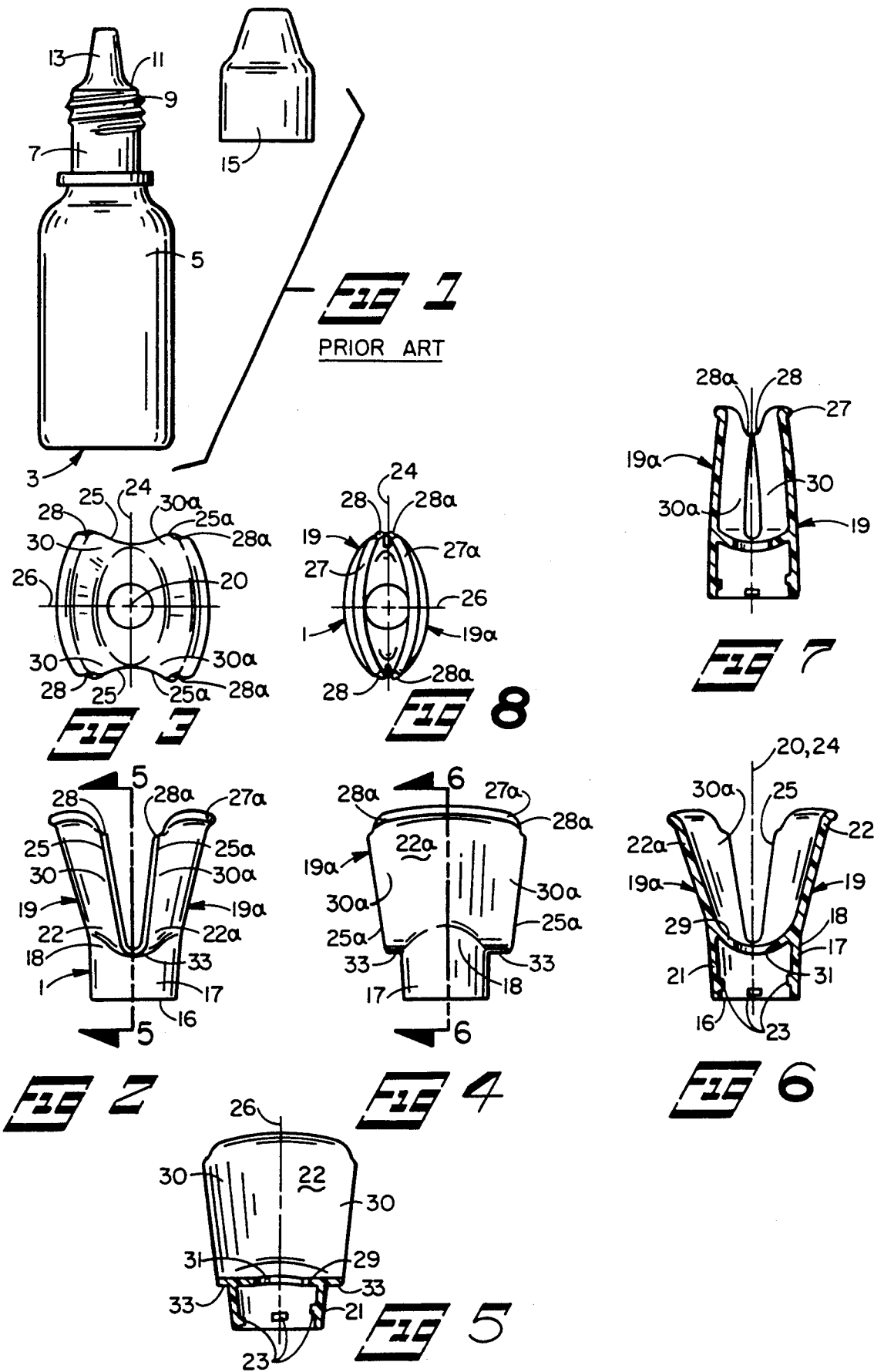

EYELID OPENER

BACKGROUND OF THE INVENTION

1. Field of the Invention

This invention pertains to ophthalmic devices, and more particularly to apparatus that aids in dispensing liquid into the eye.

2. Description of the Prior Art

It is well known to drop medicated liquids into the eye. The eyedrops may be applied for a variety of reasons ranging from merely cleaning the eyeball surface to treating serious eye diseases.

Generally, the eyedrops are contained in a soft bottle having a tip with a small opening. Holding the bottle with the tip pointing downwardly and squeezing the bottle sides causes the liquid to be expelled as individual drops or as a thin stream.

A person normally administers eyedrops to himself. To do so, he must tilt his head back, position the bottle tip vertically above the open eye, and gently squeeze the bottle. Although the procedure is simple in theory, in practice it is subject to several common and annoying problems. For one thing, the great sensitivity of the eyelid to contact by external objects makes it imperative that the bottle tip not contact an eyelash as the bottle is being squeezed, because the eye will then inadvertently close, and the drops will not fall properly into the eye. The user must also be very careful not to permit the bottle tip to touch his eyeball. Another problem is the difficulty of properly positioning the bottle tip in vertical alignment with the eye so that the drops fall properly into it. In addition, even if the bottle tip is properly positioned for dispensing drops, normal blinking action can occur just as the person squeezes the bottle such that the liquid falls on the exterior of the eyelid and is wasted.

To overcome one or more of the foregoing problems, various eyedrop dispensing devices have been developed. For example, French Patent No. 45,304 describes a combination eyelid opener and liquid holding bottle. The eyelid opener has pads on the ends of hinged levers. The bottle is held between the levers. Placing the pads on respective closed eyelids and drawing the distal ends of the levers together simultaneously opens the eyelids and squeezes the bottle. U.S. Pat. No. 4,543,096 and German Patent No. 594,860 show dispensers generally similar to that of the French Patent No. 45,304 in that squeezing pivotable levers simultaneously opens the eyelids and dispenses a drop of medicated liquid.

U.S. Pat. No. 4,386,608 describes lever like apparatus for opening the eyelids and enabling a steady stream of liquid to wash the eye for extended times. U.S. Pat. Nos. 4,792,334 and 4,946,452 show apparatus that can further open an opened eyelid to expose an ocular cul de sac. U.S. Pat. Nos. 3,598,121 and 4,605,398 teach dispensers that have limited capability of opening an eyelid and that are supported on the eyelid for properly positioning a bottle tip. U.S. Pat. Nos. 2,920,624; 3,016,898; 3,058,466; 3,934,590; 4,531,944; and 4,685,906 show various eyedrop dispensers that guide dropper bottles on the eyelid but that do not have any capabilities of opening an eyelid or of holding an eyelid open. The device of U.S. Pat. No. 3,016,898 patent is screwable onto a eyedrop bottle.

U.S Pat. No. 4,085,750 shows various embodiments of eyedrop bottle attachment in which flexible arms may be squeezed together and placed on a closed eyelid. Upon releasing the arms, their flexural strength restores them to their normal dispositions to force the eyelids apart and simultaneously guide a bottle over the eye.

Despite the variety of eyedrop dispensing aids that are presently available, there nevertheless exists a need for further development.

SUMMARY OF THE INVENTION

In accordance with the present invention, an inexpensive eyelid opener is provided that increases the convenience and reliability of dispensing liquid medicaments from ophthalmic bottles. This is accomplished by apparatus that includes a collar that engages the bottle threads and a pair of relatively wide wings flexibly joined to the collar.

The dispensing bottle with which the present invention is used has a storage chamber with a compressible wall. The chamber terminates in an elongated neck. Pressed into the free end of the neck is a tip with a small outlet hole. The neck is threaded to receive a mating cap. The cap has an elongated cavity that fits over the bottle tip.

The collar of the eyelid opener of the present invention is formed as a thin annular wall having a length approximately equal to the length of the threads on the bottle neck. The interior surface of one end of the collar wall has a number of circumferentially spaced lobes. The lobes are preferably arranged in the form of a discontinuous helix that renders the collar screwable onto the bottle threads.

Extending across the collar second end is a shoulder. The shoulder has an opening therethrough that is smaller than the bottle neck diameter and larger than the bottle tip. Consequently, the eyelid opener can be screwed onto the bottle threads until the collar shoulder abuts the free end of the bottle neck.

The wings are flexibly joined to the collar second end. The wings have thin arcuate cross sections of relatively large radius and circumferential length. The wings diverge away from the collar at a small angle. The free ends of the wings terminate in respective short outturned flanges. The flanges have a length and radius that closely conform to the size and contour of the human eyelid.

The eyelid opener is preferably manufactured from a flexible thermoplastic resin material. That material combines toughness with elasticity.

To use the eyelid opener of the present invention, its collar is screwed or pushed into the threads of the neck of a conventional ophthalmic bottle until the shoulder abuts the free end of the bottle neck. When the eyelid opener is in place on the bottle, the flanges on the ends of the wings are at a relatively great distance from the bottle tip. The two wings are squeezed together until their flanges contact each other. The flanges are placed gently but firmly on the closed eyelids of a person, and the wings are released. The elastic nature of the thermoplastic resin material in combination with the eyelid conforming design of the wing flanges causes the wings to return to their undeflected configuration and simultaneously gently open the eyelids. The wings hold the eyelids open as long as the flanges are pressed against them. With the eyelids open, the person tilts his head back and squeezes the bottle. The open eyelids assure that medicament falls properly into the eye and not on the eyelid. The relatively great distance between the wing flanges and the shoulder of the eyelid opener assures that the bottle tip does not contact the eyelashes or any other part of the eye during use.

Other advantages, benefits, and features of the invention will become apparent to those skilled in the art upon reading the detailed description of the invention.

BRIEF DESCRIPTION OF THE DRAWINGS

FIG. 1 is an exploded side view of an ophthalmic bottle with which the eyelid opener of the present invention is used.

FIG. 2 is a front view of the eyelid opener of the present invention.

FIG. 3 is a top view of the eyelid opener.

FIG. 4 is a side view of the eyelid opener.

FIG. 5 is a cross sectional view taken along lines 5—5 of FIG. 2.

FIG. 6 is a cross sectional view taken along lines 6—6 of FIG. 4.

FIG. 7 is a view similar to FIG. 6, but showing the eyelid opener in a closed configuration.

FIG. 8 is a view similar to FIG. 3, but showing the eyelid opener in the closed configuration.

DETAILED DESCRIPTION OF THE INVENTION

Although the disclosure hereof is detailed and exact to enable those skilled in the art to practice the invention, the physical embodiments herein disclosed merely exemplify the invention, which may be embodied in other specific structure. The scope of the invention is defined in the claims appended hereto.

Referring to the drawings, an eyelid opener 1 is illustrated that includes the present invention. The eyelid opener is particularly useful in conjunction with a conventional ophthalmic bottle 3 for dispensing drops of medicament from the bottle into a human eye.

The bottle 3 has a fluid containing chamber 5 and a neck 7. The neck has external threads 9 that terminate in a transverse end surface 11. From the neck end surface 11 extends a tip 13 having a small hole through which the liquid is dispensed. A cap 15 is threadable onto the bottle threads 9 to close the tip 13. The wall of the bottle chamber 5 is flexible to enable it to be squeezed and thereby force drops of ophthalmic fluid from the chamber into an open eye, not shown.

In accordance with the present invention, the eyelid opener 1 is removably attachable to the bottle 3 to aid in dispensing drops therefrom into the eye. The eyelid opener is comprised of a collar 17 and a pair of wings 19, 19a integrally joined to the collar. The collar has a first end 16, a second end 18, and a central axis 20. The central axis 20 is defined by the intersection of two orthogonal central planes 24 and 26. The collar is fabricated with a thin annular wall 21. Formed on the inner surface of the wall 21 near its first end 16 are a series of lobes 23. The lobes 23 may be arranged in a helix so as to define a discontinuous thread that is identical to the threads 9 of the bottle 3. The collar is preferably at least as long as the length of the threads on the bottle.

Integral with the collar 17 and extending across its second end 18 is a thin shoulder 29. The shoulder 29 defines an opening 31 therethrough that is smaller than the diameter of the bottle threads 9 but large enough to freely receive the bottle tip 13.

In the preferred embodiment, the wings 19, 19a are integrally joined to the collar 17 at the second end 18 thereof. The wings are symmetrical about the two central planes 24 and 26. Each wing 19, 19a is formed with a respective plate 22, 22a that has a generally arcuate cross section in a plane perpendicular to the central axis 20. The plates 22, 22a are bound by respective side edges 25, 25a, which have adjacent margins 30, 30a. The width of the plates is a little greater than the diameter of the collar 17. Consequently, the margins 30 of wing 19 blend into the associated margins 30a of the wing 19a in a pair of opposed U-shaped overhangs 33. It is preferred that the overhangs 33 are continuations of the shoulder 29. Accordingly, the shoulder may be curved in the central plane 26. The relatively wide widths of the wing plates enable them to be made with relatively thin and flexible cross sections and still be elastic, as will be discussed presently. Each plate subtends an angle somewhat less than 180 degrees about the central axis 20 near the junctions of the wings with the collar 17. The plate side edges 25, 25a converge slightly in the central plane 24 in the direction of the collar. An included angle of approximately 10 degrees between the side edges 25, 25a, of the respective plates 22, 22a, is satisfactory. Similarly, the wing plates converge in the central plane 26 in the direction of the collar; a satisfactory included angle of convergence for the plates is approximately 20 degrees. The free ends of the wing plates 22, 22a terminate in respective short outturned flanges 27, 27a. Each flange 27, 27a has respective opposite corners 28, 28a. The angle subtended by the corners 28, 28a of each wing is preferably approximately 130 degrees. A dimension of approximately 1.03 inches between the flanges 27, 27a and the shoulder 29 is satisfactory. We have found that a dimension of approximately 1.06 inches along the arcuate flanges works very well.

In FIGS. 2-6, the eyelid opener 1 is shown in an open and relaxed configuration. The eyelid opener is preferably made of a thermoplastic resin material that imparts flexible and resilient qualities to the opener. Consequently, the wings 19, 19a can be squeezed together to a closed configuration as is shown in FIGS. 7 and 8. In the closed configuration, the corners 28 of the flange 27 are in contact with the associated corners 28a of the flange 27a.

To use the eyelid opener 1 of the present invention, the cap 15 is removed from the bottle 3. The collar 17 of the eyelid opener is threaded onto the bottle threads 9 until the shoulder 29 contacts the bottle neck end surface 11. Alternately, because of the thin and flexible nature of the collar wall 21, the collar may be pushed axially onto the neck with the lobes 23 resiliently passing over and engaging the bottle neck thread 9. Then the wings 19 and 19a of the eyelid opener are squeezed together to place the eyelid opener in the closed configuration of FIGS. 7 and 8. The flanges 27 and 27a are placed gently on the person's upper and lower eyelids. Releasing the wings while holding their flanges against the eyelids enables the resilient material of the eyelid opener to return the wings to the open configuration of FIGS. 2-6, thereby opening the person,'eye. It is then merely necessary for the person to tilt his head back and squeeze the bottle chamber 5 to dispense one or more drops out the tip 13 of the bottle into the open eye. The wings of the eyelid opener are designed with sufficient length to assure that there is no likelihood that the person's eyelashes will contact the bottle tip 13 during use.

After use, the eyelid opener 1 is unscrewed or pulled from the bottle threads 9, and the bottle cap 15 is replaced. There is no need for the fingers to touch the bottle tip 13 or for the eyelid opener to touch the eye itself, so sanitary conditions are preserved.

The eyelid opener 1 is designed such that when it is in the closed configuration and the flanges 27 and 27a are placed over the eyelids of a person, the flanges extend almost completely across the respective eyelids. Consequently, only a very light pressure need be exerted on the eyelids to open them. Further, the flanges have the general profile of the eyelids and eye sockets. Accordingly, when the eyelid opener relaxes to the open configuration and opens an eye, the flanges fit comfortably within the eye socket.

Thus, it is apparent that there has been provided, in accordance with the invention, an eyelid opener that fully satisfies the aims and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

We claim:

1. An eyelid opener comprising:
   a. a collar having a central axis defined by the intersection of first and second orthogonal planes and a thin annular wall of a predetermined diameter, the collar having an internal surface that is formed with a plurality of lobes arranged in an interrupted helix;
   b. a shoulder extending across the collar, the shoulder defining an opening of predetermined size therethrough; and
   c. first and second opposed wings generally symmetrical about the first and second orthogonal planes and having respective plates that have oppositely extending first ends and free ends, the plates being joined at their respective first ends to the collar, the free ends of the plates terminating in oppositely facing flanges that are normally spaced a predetermined distance apart in an open configuration, each wind plate having a generally arcuate cross section in a plane perpendicular to the central axis, the flanges having lengths and curvatures that conform to the size and contour of substantially the entire length of the exterior of the human eyelid, the winds being made of resilient material so that the wings are squeezable together to bring the flanges thereof adjacent each other to a closed configuration and returnable to the open configuration when the wings are released.

2. The eyelid opener of claim 1 wherein the wind flanges have arcuate lengths of approximately 1.06 inches, and wherein the wing flanges subtend respective angles of approximately 130 degrees about the central axis when the wings are in the open configuration.

3. The eyelid opener of claim 1 wherein each wing plate is partially defined by a pair of side edges that extend between the plate first end and free end and that are spaced apart a distance greater than the diameter of the collar, plate margins adjacent the respective side edges of the first plate at the first end thereof joining the associated plate margins adjacent the respective side edges of the second plate at the first end thereof to thereby create first and second opposed overhangs of the plate margins adjacent the collar.

4. The eyelid opener of claim 3 wherein the side edge of each plate converge toward the collar.

5. The eyelid opener of claim 1 wherein the shoulder is curved in the plane of the second orthogonal plane.

6. The eyelid opener of claim 1 wherein each plate is partially defined by a pair of side edges that extend between the plate first end and free end and are spaced apart at the first end of the plate a distance at least at great as the diameter of the collar.

7. In combination with an ophthalmic bottle having a fluid holding chamber; a neck connected to the chamber and terminating in an end surface, the neck being threaded adjacent the end surface thereof; and a tip extending from the neck end surface, the bottle having a central axis formed by the intersection of first and second orthogonal planes, an eyelid opener comprising:
   a. collar means having a predetermined diameter generally concentric with the bottle central axis for removably engaging the threads on the bottle neck; and
   b. a pair of wings symmetrical about the first and second orthogonal planes and having widths greater than the diameter of the collar means, the wings having respective first ends joined to the collar means and respective second ends, the first ends of the wings being joined to each other in a shoulder that extends across the collar means and in opposed generally U-shaped overhangs that are coplanar with the shoulder, the shoulder defining a hole therethrough sized to receive the bottle tip, the second ends of the wings terminating in outturned flanges sized and shaped to conform to substantially the contour of the human eyelid.

8. The eyelid opener of claim 7 wherein the collar means comprises:
   a. a thin annular wall having first and second ends and sized to received the bottle threads; and
   b. a plurality of lobes formed on the annular so that the lobes enable the collar to be screwed on to the bottle threads.

9. The eyelid opener of claim 7 wherein the wings are bounded by respective side edges that converge in the direction of the collar means.

* * * * *